United States Patent [19]

Kitaura et al.

[11] Patent Number: 4,497,729
[45] Date of Patent: Feb. 5, 1985

[54] PEPTIDE, PROCESS FOR PREPARATION THEREOF AND USE THEREOF

[75] Inventors: Yoshihiko Kitaura, Sakurai; Osamu Nakaguchi, Toyonaka; Keiji Hemmi, Suita; Satoshi Yonishi, Kadoma; Hidekazu Takeno, Tenri, all of Japan

[73] Assignee: Fujisawa Pharmaceutical Co., Ltd., Osaka, Japan

[21] Appl. No.: 322,902

[22] Filed: Nov. 19, 1981

[30] Foreign Application Priority Data

Dec. 1, 1980 [GB] United Kingdom ............... 8038509
Apr. 13, 1981 [GB] United Kingdom ............... 8111584

[51] Int. Cl.³ .......................................... C07C 103/52
[52] U.S. Cl. .............................................. 260/112.5 R
[58] Field of Search .................. 424/177; 260/112.5 R

[56] References Cited

U.S. PATENT DOCUMENTS 4,261,979  4/1981  Jolles et al. ................... 260/112.5 R
4,311,640  1/1982  Kuroda et al. ................ 260/112.5 R
4,399,066  8/1983  Nakaguchi et al. .......... 260/112.5 R

FOREIGN PATENT DOCUMENTS 0003833  2/1979  European Pat. Off. .
2033906  5/1980  United Kingdom .
2053231  2/1981  United Kingdom .

OTHER PUBLICATIONS

Ariëns, Drug Design, vol. II, N.Y., Academic Press, 1971, pp. 338–341, 355, 360–362.
Dezelee et al., Biochemistry, vol. 9, No. 4, 1970, pp. 823–831.
Kitaura et al., "European Patent Application", Ser. No. 0,011,283, 5-20-80.
Biochemistry, vol. 9, No. 4, 1970, pp. 823–831, Dezelee et al.
Biochemical and Biophysical Research Communications, vol. 59, No. 4, 1979, pp. 1317–1325, (Ellouz et al.).
Agricultural and Biological Chemistry, 41(5), 1977, pp. 763–768, (Nakamura et al.).
Abstracts of the Eleventh International Congress on Chemotherapy, Oct. 1–5, 1979, Abstract-702, (Werner et al.).
11th International Congress of Chemotherapy, 19th Interscience Conference on Antimicrobial Agents and Chemotherpay-Oct. 1979, Werner et al.-Immunopotentiating Activities of Microbial Tetrapeptides after Coupling with Lauric Acid.

Primary Examiner—Delbert R. Phillips
Assistant Examiner—F. Moezie
Attorney, Agent, or Firm—Oblon, Fisher, Spivak, McClelland & Maier

[57] ABSTRACT

This invention relates to novel peptides, of pharmacological activity, of the formula:

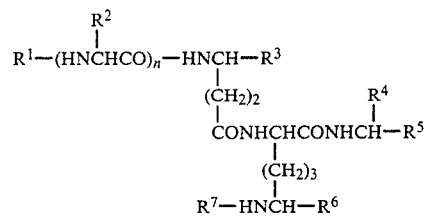

wherein
$R^1$ is heptanoyl, stearoyl, 2-hydroxypropionyl or 2-acetoxypropionyl,
$R^2$ is hydrogen or methyl,
$R^3$ is carboxy, benzyloxycarbonyl or hydroxymethyl,
$R^4$ is hydrogen or methyl,
$R^5$ is carboxy or hydroxymethyl,
$R^6$ is carboxy, methoxycarbonyl, 3-t-butoxycarbonylcarbazoyl or hydroxymethyl,
$R^7$ is hydrogen, 3-t-butoxycarbonyl or benzyloxycarbonyl, and
n is an integer 0 or 1, with the proviso that when each of $R^3$ and $R^6$ is not simultaneously hydroxymethyl, then $R^5$ is hydroxymethyl.

9 Claims, No Drawings

PEPTIDE, PROCESS FOR PREPARATION THEREOF AND USE THEREOF

This invention relates to a new peptide. More particularly, this invention relates to a new peptide and the pharmaceutically acceptable salt thereof, which have pharmacological activities, to processes for the preparation thereof and to a new intermediate for preparing the active peptide, and to the pharmaceutical composition comprising the same and a method of use thereof.

A new peptide of this invention is represented by the following formula (I):

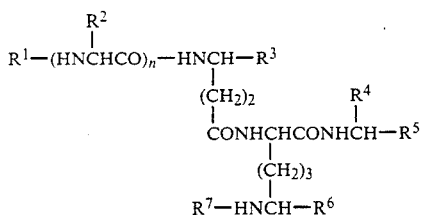

wherein
$R^1$ is hydrogen or acyl,
$R^2$ and $R^4$ are each hydrogen or lower alkyl,
$R^3$ and $R^6$ are each carboxy, protected carboxy, carbamoyl or hydroxymethyl,
$R^5$ is hydrogen, carboxy, protected carboxy, carbamoyl, carboxy or protected carboxy(lower)alkyl, or hydroxy(lower)alkyl,
$R^7$ is hydrogen or an amino protective group, and
n is an integer 0 or 1,
with proviso that in the restricted case that each of $R^3$ and $R^6$ is not simultaneously hydroxymethyl, $R^5$ should be always hydroxy(lower)alkyl.

Particulars of the various definitions, which are mentioned hereinabove and hereinafter, and preferred examples thereof are explained in the following.

The term "lower" is intended to mean a group having 1 to 8 carbon atoms, unless otherwise provided.

(1) Re. Acyl for $R^1$ and $R_a^1$:
As suitable examples of acyl, there may be exemplified alkanoyl, aralkanoyl or the like.

As suitable example of alkanoyl, there may be exemplified acetyl, propionyl, butyryl, isobutyryl, valeryl, isovaleryl, pivaloyl, hexanoyl, α-ethylhexanoyl, heptanoyl, octanoyl, lauroyl, stearoyl, n-docosanoyl and the like.

In the above exemplified alkanoyls, the aliphatic hydrocarbon moiety may have optionally one or more suitable substituent(s) such as amino, halogen (e.g. fluorine, chlorine, bromine, etc.), hydroxy, carboxy and the like. As suitable alkanoyls having such a substituent, there may be exemplified hydroxy(lower)alkanoyl such as 2-hydroxypropionyl (e.g. lactoyl).

As suitable example of aralkanoyl, there may be exemplified ar(lower)alkanoyl such as phenyl(lower)alkanoyl (e.g. phenylacetyl, etc.) or the like.

In the above exemplified aralkanoyl, the aromatic hydrocarbon moiety and/or the aliphatic hydrocarbon moiety may have optionally one or more suitable substituent(s), such as the same as those exemplified as the suitable substituent for the alkanoyl.

Among said substituted aralkanoyl, as suitable examples there may be exemplified phenyl(lower)hydroxyalkanoyl such as mandelyl and the like.

In the above exemplified acyl, in case that said acyl has one or more functional group(s) such as hydroxy, amino and carboxy, such a functional group may be protected by a conventional protective group to form protected hydroxy, protected amino and protected carboxy.

(2) Re. Lower alkyl for $R^2$ and $R^4$:
Suitable example of lower alkyl is one having 1 to 6 carbon atoms such as methyl, ethyl, propyl, isopropyl, butyl, isobutyl, pentyl, isopentyl and the like.

(3) Re. Protected carboxy for $R^3$, $R_a^3$, $R^5$ and $R^6$ and functional group in the acyl for $R^1$ and $R_a^1$, and protected carboxy moiety for $R^5$:
A protective group of the protected carboxy includes a conventional carboxy protective group which is conventionally used in the field of amino acid and peptide chemistry.

As suitable examples of protected carboxy, there may be exemplified an ester such as an ester with silyl compound, an ester with an aliphatic hydroxy compound and an ester with a hydroxy compound containing an aromatic group, and a protected carbazoyl of the formula: —CONHNHY (wherein Y is hydrogen or an amino protective group).

As more suitable examples of protected carboxy, there may be exemplified alkyl such as lower alkyl (e.g. methyl, ethyl, etc.) ester, aralkyl such as mono- or diphenyl(lower)alkyl (e.g. benzyl, diphenylmethyl, etc.) ester and the like.

(4) Re. Protected carboxy excepting esterified carboxy for $R_b^3$, $R_c^3$, $R_a^5$, $R_b^5$, $R_a^6$ and $R_b^6$, and protected carboxy excepting esterified carboxy moiety for $R_a^5$ and $R_b^5$:
As suitable example of protected carboxy excepting esterified carboxy, there may be exemplified a protected carbazoyl of the formula: CONHNHY (wherein Y is hydrogen or or an amino protective group) or the like.

(5) Re. Esterified carboxy for $R_b^3$, $R_a^5$ and $R_a^6$, and esterified carboxy moiety for $R_a^5$:
Esterified carboxy includes a conventional one and there may be exemplified, as suitable examples, the same esters as illustrated above for explanation of protected carboxy.

(6) Re. Amino protective group for $R^7$, $R_a^7$ and Y, and the functional group in the acyl group for $R^1$ and $R_a^1$:
The amino protective group includes a conventional amino protective group which is used in the field of amino acid and peptide chemistry.

As suitable examples of the amino protective group, there may be exemplified alkoxycarbonyl such as lower alkoxycarbonyl (e.g. methoxycarbonyl, ethoxycarbonyl, propoxycarbonyl, butoxycarbonyl, t-butoxycarbonyl, t-pentoxycarbonyl, etc.), aralkoxycarbonyl such as phenyl(lower)alkoxycarbonyl (e.g. benzyloxycarbonyl, etc.) and the like.

(7) Re. Hydroxy protective group in the acyl for $R^1$ and $R_a^1$:
As suitable example of a hydroxy protective group in the acyl group for $R^1$ and $R_a^1$, there may be exemplified a conventional one, for example, acyl such as alkanoyl (e.g. acetyl, etc.).

(8) Re. Hydroxy(lower)alkyl for $R^5$, $R_a^5$ and $R_b^5$:
Suitable example of hydroxy(lower)alkyl is one having 1 to 6 carbon atoms such as methyl, ethyl, propyl, isopropyl, butyl, isobutyl, pentyl, isopentyl, the optional carbon atom(s) of which is substituted by hydroxy.

Among such a hydroxy(lower)alkyl, as more suitable example, there may be exemplified hydroxymethyl, hydroxyethyl, hydroxypropyl, or the like.

(9) Re. Carboxy- or protected carboxy(lower)alkyl for $R^5$, $R_a^5$, $R_b^5$ and $R_c^5$:

Suitable example of carboxy- or protected carboxy(lower)alkyl is one having 1 to 6 carbon atoms such as methyl, ethyl, propyl, isopropyl, butyl, isobutyl, pentyl or isopentyl, the optional carbon atom(s) of which is substituted by carboxy or protected carboxy.

(10) Re. Protected carboxy excepting esterified carboxy(lower)alkyl for $R_a^5$ and $R_b^5$:

Suitable example of protected carboxy excepting esterified carboxy(lower)alkyl is one having 1 to 6 carbon atoms such as methyl, ethyl, propyl, isopropyl, butyl, isobutyl, pentyl or isopentyl, the optional carbon atom(s) of which is substituted by protected carboxy excepting esterified carboxy(lower)alkyl.

(11) Re. Esterified carboxy(lower)alkyl for $R_a^5$:

Suitable example of esterified carboxy(lower)alkyl is one having 1 to 6 carbon atoms such as methyl, ethyl, propyl, isopropyl, butyl, isobutyl, pentyl or isopentyl, the optional carbon atom(s) of which is substituted by esterified carboxy.

A pharmaceutically acceptable salt of the new peptides of the formula (I) may include a salt with an inorganic or organic base such as an alkali metal salt (e.g. sodium salt, potassium salt, etc.), an alkaline earth metal salt (e.g. calcium salt, etc.), ammonium salt, organic amine salt (e.g. ethanolamine salt, triethylamine salt, dicyclohexylamine salt, etc.) or the like, and an acid addition salt with organic or inorganic acid such as methane sulfonate, hydrochloride, sulfate, nitrate, phosphate or the like.

The compound (I) of this invention can be prepared by various methods, details of which will be apparent from the following descriptions.

(1) Process 1: Peptide bond formation

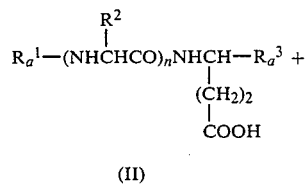

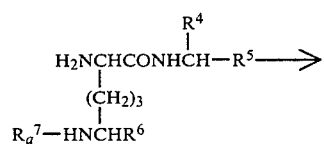

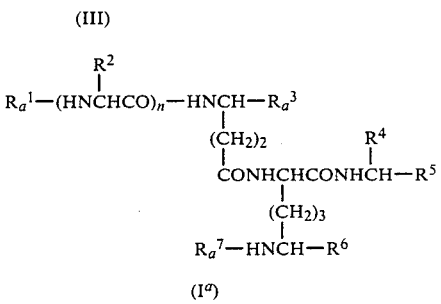

In the above formulae, $R_a^1$ is acyl, $R_a^3$ is protected carboxy, carbamoyl, hydroxymethyl, $R_a^7$ is an amino protective group, and $R^2$, $R^4$, $R^5$, $R^6$ and n are each as defined above, with proviso that in the restricted case that each of $R_a^3$ and $R^6$ is not simultaneously hydroxymethyl, $R^5$ should be hydroxy(lower)alkyl.

(2) Process 2:

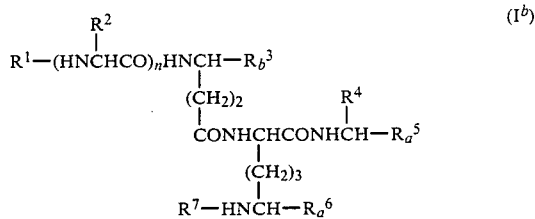

wherein $R_b^3$ and $R_a^6$ are each carboxy, protected carboxy excepting esterified carboxy, esterified carboxy, carbamoyl or hydroxymethyl, $R_a^5$ is hydrogen, carboxy, protected carboxy excepting esterified carboxy, esterified carboxy, carbamoyl, carboxy(lower)alkyl, protected carboxy excepting esterified carboxy(lower)alkyl, esterified carboxy(lower)alkyl or hydroxy(lower)alkyl, and $R^1$, $R^2$, $R^4$, $R^7$ and n are each defined above, with proviso that at least one of $R_b^3$ and $R_a^6$ is always esterified carboxy, or $R_a^5$ is esterified carboxy or esterified carboxy(lower)alkyl.

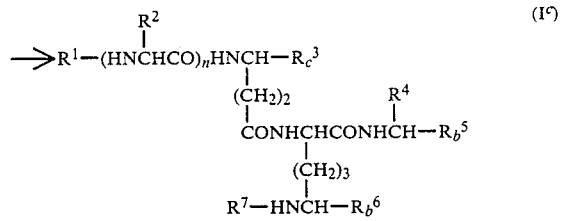

wherein $R_c^3$ and $R_b^6$ are each carboxy, protected carboxy excepting esterified carboxy, carbamoyl or hydroxymethyl, $R_b^5$ is hydrogen, carboxy, protected carboxy excepting esterified carboxy, carbamoyl, carboxy(lower)alkyl or protected carboxy excepting esterified carboxy(lower)alkyl or hydroxy(lower)alkyl, and $R^1$, $R^2$, $R^4$, $R^7$ and n are each as defined above, with proviso that at least one of $R_c^3$ and $R_b^6$ is always hydroxymethyl, or $R_b^5$ is hydroxy(lower)alkyl.

(3) Process 3:

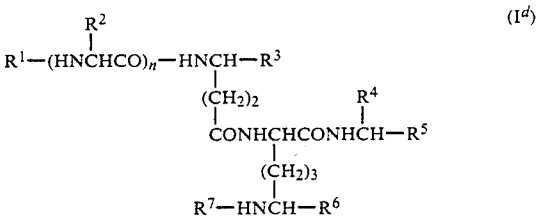

wherein $R^1$, $R^2$, $R^3$, $R^4$, $R^5$, $R^6$, $R^7$ and n are each as defined above, with proviso that at least one of $R^3$ and $R^6$ is protected carboxy, or $R^5$ is protected carboxy or protected carboxy(lower)alkyl, or $R^7$ is an amino protective group.

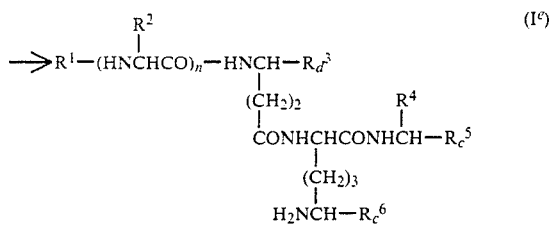
(I$^c$)

wherein $R_d^3$ and $R_c^6$ are each carboxy, carbamoyl or hydroxymethyl, $R_c^5$ is hydrogen, carboxy, carbamoyl, carboxy(lower)alkyl or hydroxy(lower)alkyl, and $R^1$, $R^2$, $R^4$ and n are each as defined above, with proviso that in the restricted case that each of $R_d^3$ and $R_c^6$ is not simultaneously hydroxymethyl, $R_c^5$ is always hydroxy(lower)alkyl.

Detailed explanation of processes for preparing of the compound (I) will be made in the following:

(1) Process 1: Peptide bond formation Compound (II) + Compound (III)→Compound (Ia)

This process relates to a method for preparing Compound (Ia) by reacting Compound (II) or its salt with a Compound (III) or its salt.

The reaction of this process can be conducted as follows. That is, in one case, as the first step, the carboxy group of Compound (II) or its salt is usually activated in a conventional manner, for example, in the form of its acid halide, azide, acid anhydride or a mixed anhydride, activated ester, and the like, and is reacted with the Compound (III) to give Compound (Ia), and in the other case, the Compound (II) or its salt is reacted with the Compound (III) or its salt directly in the presence of a conventional condensing agent such as N,N-dicyclohexylcarbodiimide and the like. Among these activation methods, preferred activation method for the carboxy group of the Compound (II) into its activated form and preferred condensing agent as mentioned above are selected according to kinds of the carboxy protective group(s) of the Compound (II) and (III) and to the reaction conditions (e.g. the kinds of the reaction solvent, reaction temperature and so on).

This reaction is preferably carried out in a solvent such as methylene chloride, chloroform, tetrahydrofuran, dioxane, ethyl acetate, methanol, ethanol, water or the like under at −20° C. t to at ambient temperature and the reaction in the presence of a condensing agent is usually carried out in an anhydrous, but not critical conditions.

(2) Process 2: Compound (I$^b$)→Compound (I$^c$)

This process relates to a method for preparing Compound (I$^c$) or its salt by reacting Compound (I$^b$) or its salt with a reducing agent.

The reduction can be carried out in a conventional manner which can be applied to reduction of a esterified carboxy group into hydroxymethyl and particularly, the reduction is carried out by using a reducing agent such as alkali metal borohydride (e.g. lithium borohydride, lithium cyanoborohydride, sodium borohydride, potassium borohydride, sodium cyanoborohydride, etc.) or the like.

The reduction is usually carried out in a conventional solvent such as methanol, ethanol, dioxane, tetrahydrofuran or the like under ice-cooling to at ambient temperature.

In this process, in case that the acyl group for $R^1$ has one or more protective group(s) for hydroxy, amino and (or) carboxy, such a protective group(s) may be simultaneously removed in this process.

(3) Process 3: Elimination of protective group(s) Compound (I$^d$)→Compound (I$^e$)

This process relates to a method for preparing Compound (I$^e$) or its salt by subjecting Compound (I$^d$) or its salt to elimination reaction of protective group(s) of protected carboxy for $R^3$ and (or) $R^5$ and (or) $R^6$, and (or) amino protective group for $R^7$, detailed explanation for which is as follows:

Process 3-1: Elimination of an amino protective group for $R^7$

This process can be applied to case that the amino protective group for $R^7$ reveals a chemically different behavior from that of the acyl group for $R^1$ against each kind of the elimination methods to be employed, that is, the case that the amino protective group can be eliminated, but the acyl group for $R^1$ is not eliminated according to the elimination method as employed.

This reaction is carried out by conventional methods such as catalytic reduction method, liquidammoniaalkalimetal method, acid method, zinc acid method, base method, hydrazine method and the like.

Among these methods, preferred one is selected according to kind of the amino protective group for $R^7$, and also to the chemically defferent behavior of said amino protective group from the acyl for $R^1$ as explained above.

Among the above elimination methods, an acid method is employed as the most convenient and conventional one and said method is explained as follows:

This reaction is conventionally carried out in a solvent such as methylene chloride, chloroform, acetic acid, water and the like in the presence of inorganic or organic acid such as trifluoroacetic acid, formic acid, p-toluenesulfonic acid, hydrochloric acid, hydrobromic acid and the like, and anisole is preferably added thereto.

Among the exemplified acid, trifluoroacetic acid and formic acid are also used as the solvent.

This reaction is usually carried out under ice-cooling to an ambient temperature.

Process 3-2: Elimination of carboxy protective group of protected carboxy for $R^3$, $R^5$ and $R^6$ The reaction for elimination of protective group of the protected carboxy group is carried out by a conventional method such as hydrolysis and reduction or the like, details of whcih are explained in the following.

(i) For hydrolysis which refers to the same meaning as solvolysis including, for example, acidolysis, alcoholysis, aminolysis, hydroxinolysis, etc.:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion exchange resin and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline, N,N-dimethylaniline, etc.), a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.) or the like; a basic ion-exchange resin and the like.

The hydrolysis is preferably conducted under somewhat milder conditions such as cooling or warming and usually in a solvent which does not have adverse influence to the reaction, e.g. water, a hydrophilic solvent such as alcohol (e.g. methanol, ethanol, propanol, etc.), acetone, N,N-dimethylformamide, tetrahydrofuran, dioxane, dimethylsulfoxide, etc. or a mixture thereof, and other hydrophobic solvent such as benzene, diethylether, etc. may also be used as a solvent. A liquid abovementioned acid or base can also be used as solvent.

(ii) For reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) or the like.

The reduction is usually carried out in a solvent. A suitable solvent to be used may be e.g. water, alcohol (e.g. methanol, ethanol, propanol, etc.) and other conventional organic solvent or a mixture thereof. Additionally, the afore-mentioned liquid acids to be used in chemical reduction can also be used as solvent. Further, a suitable solvent to be used in catalytic reduction may be, e.g. the above-mentioned solvent, and other conventional solvent, such as diethyl ether, dioxane, tetrahydrofuran, etc., or a mixture thereof.

The reaction is preferably carried out under somewhat milder conditions such as cooling or warming.

Process 3-3: Removal of hydrozino group

A protective group of a protected carbazoyl of the formula: —CONHNHY (wherein Y is hydrogen or an amino protective group) can be removed by subjecting Compound (I$^d$) at first to the reaction of Process 3-1 for eliminating an amino protective group (i.e. Y) to give —CONHNH$_2$ group and then subjecting the reaction product to the reaction of this step to give —COOH group, and particular of this reaction step is as follow.

The reaction of this step is carried out in a conventional manner by treating the Compound (I$^d$) with a conventional oxidizing agent which is capable of oxidizing a group of the formula: —CONHNH$_2$ to form into a group of the formula: —COOH and accordingly preferred example of such an oxidizing agents may be halogen such as iodine, bromine etc., perhalogenic acid such as periodic acid or its salt (e.g. sodium salt, potassium salt, etc.), perchloric acid, etc., N-haloimide such as N-bromosuccinimide, etc., lead tetraacetate, hydrogen peroxide or its salt (e.g. nickel peroxide, etc.), metal oxide such as mercuric oxide, manganese dioxide, nickel peroxide, etc., cupric compound (e.g. cupric acetate, cupric sulfate, etc.) and the like.

This reaction is usually carried out in a solvent such as water, acetic acid, methanol, ethanol, tetrahydrofuran, dioxane and the like and a mixture thereof, which should be appropriately selected in accordance with the kind of oxidizing agent to be used.

This reaction is usually carried out under ice-cooling to an ambient temperature, or under reflux.

Among these methods for elimination of protective groups, preferred one and appropriate combination methods are to be selected according to kinds of the protective groups of carboxy group and amino protective group to be removed off.

It is noted that this process includes the following cases of eliminatiin of protective groups of protected carboxy and amino protective group, that is, one case that all of the carboxy protective groups for $R^3$, $R^5$ and $R^6$ and the amino protective group for $R^7$ in the Compound (I$^d$) are simultaneously removed by a method to be employed to the reaction, and the other case that the carboxy protective groups and the amino protective group are sequentially and stepwise removed by a method which is appropriately selected according to the kinds of the protective group to be removed.

As to Process 3 for elimination of protective group(s) (i.e. Process 3-1 and 3-2 and 3-3), the followings are to be noted. That is, in case that acyl for $R^1$ has one or more protective group(s) for hydroxy, amino and (or) carboxy, such as amino protective group and carboxy protective group among said protective group may be simultaneously removed in this process, and such a hydroxy protective group such as alkanoyl (e.g. acetyl, etc.) may be previously removed by subjecting the compound (I$^d$) to elimination reaction of hydroxy protective group in a conventional manner such as reduction as illustrated in the Process 3-2.

The starting Compounds (II) and (III) include known compounds (e.g. European Patent publication No. 11283) and new compounds. Said new compounds can be prepared, for example, by methods as described below.

(1) Process 1$^s$:

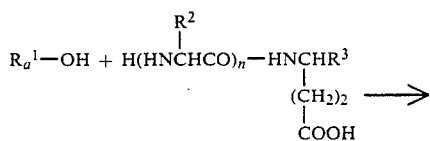

(II-1)

-continued $$R_a{}^1-(HNCHCO)_n-HNCHR^3$$
with $R^2$ on the first CH and $(CH_2)_2$—COOH branch
(II-2)

(2) Process $2^s$:

$$R_a{}^1(HNCHCO)_nOH + H_2NCHR^3$$
(IV) with $R^2$ ; (V) with $(CH_2)_2$—COOH
$\longrightarrow$ $$R_a{}^1(HNCHCO)_n-HNCHR^3$$
with $R^2$ and $(CH_2)_2$—COOH
(II-2)

(3) Process $3^s$:

$$R_a{}^7NHCHCOOH \quad + \quad H_2NCH-R^5 \longrightarrow$$
with $(CH_2)_3$—$R_b{}^7HNCHR_d{}^6$ ; with $R^4$
(III-1) (VI)

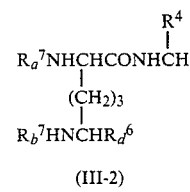

(III-2)

(4) Process $4^s$:

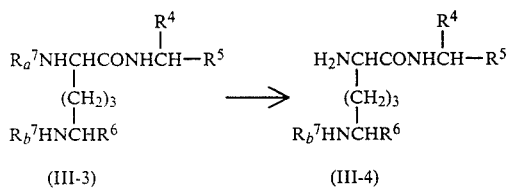

(III-3) (III-4)

(5) Process $5^s$:

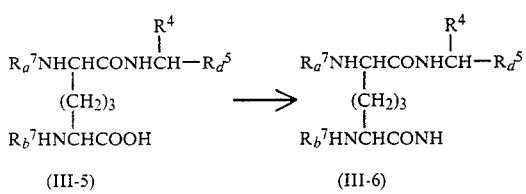

(III-5) (III-6)

(6) Process $6^s$:

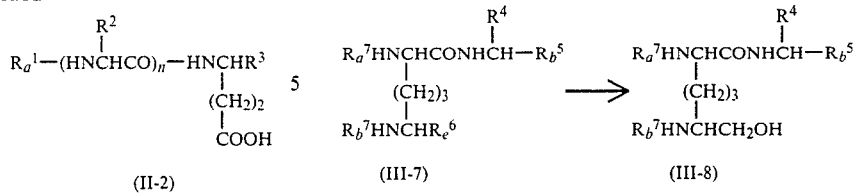

(III-7) (III-8)

In the above formulae, $R_d{}^6$ is protected carboxy, carbamoyl or hydroxymethyl, $R_b{}^7$ is an amino protective group, $R_d{}^5$ is the same as defined in $R^5$ excepting carboxy and carboxy(lower)alkyl, $R_e{}^6$ is esterified carboxy and $R_a{}^1$, $R^2$, $R^3$, $R^4$, $R^5$, $R_b{}^5$, $R^6$, $R_a{}^7$ and n are each as defined above.

(1) Process $1^s$: Compound (II-1) $\xrightarrow{R_a{}^1-OH}$ Compound (II-2)

This process relates to a method for preparing Compound (II-2) by reacting Compound (II-1) with an acylating agent.

The acylating agent to be used in this reaction includes an organic carboxylic acid ($R_a{}^1$-OH wherein $R_a{}^1$ is an acyl group) and its reactive derivative. Suitable examples of said acid are the corresponding organic carboxylic acid to that comprising the acyl group as exemplified hereinabove in details in the descriptions of suitable examples of the acyl group for $R^1$ and $R_a{}^1$ of the Compound (I).

Said organic carboxylic acid as an acylating agent can be used as its reactive derivative. As such reactive derivatives, there may be exemplified conventional one such as an acid halide, an acid azide, an acid anhydride, an activated amide, an activated ester or the like.

In the reaction, when a free acid is used as an acylating agent, the acylation reaction may preferably be conducted in the presence of a conventional condensing agent.

The reaction is usually conducted in a conventional solvent under ice-cooling ~ at ambient temperature, and preferably conducted in the presence of a conventional base.

(2) Process $2^s$: Compound (IV)+Compound (V)$\rightarrow$Compound (II-2)

This process relates to a method for preparing Compound (II-2) or its salt by reacting Compound (IV) or its salt with Compound (V) or its salt.

The reaction is carried out substantially in the same manner as Process 1.

(3) Process $3^s$: Compound (III-1)+Compound (VI)$\rightarrow$Compound (III-2)

This process relates to a method for preparing Compound (III-2) or its salt by reacting Compound (III-1) with Compound (VI) or its salt.

The reaction is carried out substantially in the same manner as Process 1.

(4) Process $4^s$: Compound (III-3)$\rightarrow$Compound (III-4)

This process relates to a method for preparing Compound (III-4) or its salt by subjecting Compound (III-3) or its salt to elimination reaction of an amino protective group for $R_a{}^7$.

This process can be applied to case that the amino protective group for $R_a{}^7$ reveals a chemically different behavior from that of the amino protective group for $R_b{}^7$ against each kind of the elimination methods to be employed.

The reaction is carried out substantially in the same manner as Process 3-1.

(5) Process 5⁵: Compound (III-5)→Compound (III-6)

This process relates to a method for preparing Compound (III-6) or its salt by subjecting Compound (III-5) or its salt to an amidation reaction.

The reaction is usually carried out as a first step by activating the carboxy group of the Compound (III-5) in a conventional manner, for example, in a form of its activated ester, and then reacting the resulting compound with ammonia.

The reaction is preferably carried out in a solvent such as methylene chloride, chloroform or the like under ice-cooling to at ambient temperature.

(6) Process 6⁵: Compound (III-7)→Compound (III-8)

This process relates to a method for preparing Compound (III-8) or its salt by reacting Compound (III-7) or its salt with a reducing agent.

The reaction is carried out substantially in the same manner as Process 2.

As to the object compound (I) and starting compounds (II) and (III) which are prepared according to the aforementioned Processes, it is to be noted that each of said compounds includes one or more stereoisomers which is due to the asymmetric carbon atoms in their molecule and all of such isomers are included within the scope of this invention.

The new peptide (I) and its pharmaceutically acceptable salts of this invention have been found to possess protective efficacy in experimental infection.

Accordingly, the new peptide (I) and its pharmaceutically acceptable salts are useful for the therapeutic treatment of infectious diseases caused by pathogenic microorganism, especially gram-negative bacteria and gram-positive bacteria and fungi.

Further, Compounds (II) and (III) are useful as intermediate for preparing Compound (I) having biologically active properties as mentioned above.

For the purpose of showing pharmaceutical utility of the new peptide (I), pharmacological test data thereof are illustrated in the following.

PROTECTIVE EFFICACY IN EXPERIMENTAL INFECTION IN MICE

In determining the protective efficacy against experimental infections in mice, the test compound was dissolved in and diluted with sterile saline to provide prescribed concentrations of drug.

Male ICR-strain mice, aged 4 weeks were used in groups of ten mice, *E. coli* 22 was cultivated overnight at 37° C. on trypticase soy agar and then were suspended in a sterile saline to obtain microbial cell concentration of $2.6 \times 10^9$ CFU/ml. Mice were inoculated intraperitoneally with $8.7 \times 10^7$ CFU/mouse. Each of the test drugs was given intraperitoneally in various doses to a group of ten mice four days before challenge.

Survival percent were found from the number of the surviving animals after three days of injection, Results are shown in Table

| Test Compound (Example No.) | Survival (%) | | |
|---|---|---|---|
| | Dose 0.1 mg/kg | Dose 0.01 mg/kg | Control |
| Example 1 (Step 2) | 100 | — | 10 |
| Example 2 (Step 2) | 50 | 60 | 10 |
| Example 3 | 50 | — | 10 |

-continued

| Test Compound (Example No.) | Survival (%) | | |
|---|---|---|---|
| | Dose 0.1 mg/kg | Dose 0.01 mg/kg | Control |
| Example 5 (Step 2) | 90 | 80 | 20 |
| Example 6 (Step 2) | 80 | 100 | 10 |
| Example 7 (Step 3) | 70 | 50 | 10 |
| Example 8 | — | 60 | 10 |
| Example 9 | 80 | 50 | 10 |

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily doese of about 0.1–100 mg of the active ingredient/kg of a human being or an animal is generally give for treating diseases, and an average, single dose of about 50 mg, 100 mg, 250 mg, and 500 mg is generally administered.

The following examples are given for purpose of illustrating this invention.

In the following examples, starting compounds and object compounds are expressed by using the following abbreviations:

Su: N-hydroxysuccimide
Lac: Lactoyl
Ala: Alanyl
Glu: Glutamyl
Gly: Glycyl
DAP: α, ε-Diaminopimelyl
Z: benzyloxycarbonyl
Boc: t-butoxycarbonyl
Bzl: Benzyl
Ac: acetyl

Preparation 1

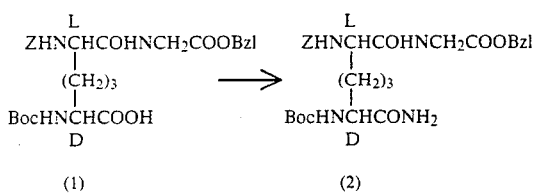

To a mixture of Z-(L)-Boc-(D)-mesoDAP-(L)-GLyOBzl (1)(3.95 g) and N-methylmorpholine (0.85 g) in dry methylene chloride (70 ml) was added isobutyl chloroformate (0.95 g) at −10∼−15° C. and the mixture was stirred for 30 minutes at the same temperature. The mixture was then cooled to −40° C. and 2N solution (15 ml) of ammonia in ethanol was added. After stirring for 30 minutes at the same temperature, the mixture was concentrated and the residue was dissolved in ethyl acetate, washed with water, dried over magnesium sulfate, and evaporated to give an oil, which was pulverized with ether to give Z-(L)-Boc-(D)-mesoDAP-(D)-NH$_2$-(L)-GlyOBzl (2)(3.1 g).

IR (Nujol): 3300, 1735, 1685, 1655 cm$^{-1}$.

NMR (CD$_3$OD): δ1.48 (9H, s), 1.4–2.0 (6H, m), 4.03 (2H, s), 3.9–4.3 (2H, m), 4.13 (2H, s), 4.22 (2H, s), 7.40 (10H, s).

Preparation 2

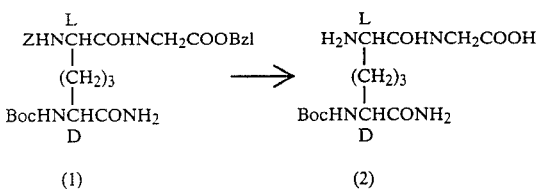

To a solution of Z-(L)-Boc-(D)-mesoDAP-(D)-NH$_2$-(L)-GlyOBzl (1)(2.7 g) in a mixture of methanol (75 ml) and water (10 ml) was added 10% palladium-charcoal (1.0 g) and the mixture was hydrogenated under an atmospheric pressure of hydrogen. After removal of the catalyst, the filtrate was evaporated to dryness. The residue was pulverized with ether to give Boc-(D)-mesoDAP-(D)-NH$_2$-(L)-GlyOH (2)(1.59 g).

IR (Nujol): 3600–2200, 1690 (sh), 1670 cm$^{-1}$.

NMR (CD$_3$OD): δ1.42 (9H, s), 1.2–2.0 (6H, m), 3.6–4.1 (4H, m).

Preparation 3

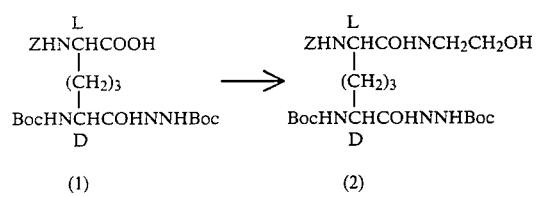

To a mixture of Z-(L)-Boc-(D)-mesoDAP-(D)-NHNHBoc (1)(5.38 g) and N-methylmorpholine (1.01 g) in dry methylene chloride (100 ml) was added isobutyl chloroformate (1.37 g) at −10∼−15° C. and the mixture was stirred for 30 minutes at the same temperature. A solution of ethanolamine (0.61 g) in dry methylene chloride (6 ml) was added and the mixture was stirred for 2 hours at the same temperature. After evaporation of the solvent, the residue was dissolved in ethyl acetate (70 ml) and washed successively with 2.5% hydrochloric acid, water, 2.5% sodium bicarbonate and water. During over magnesium sulfate and evaporation gave an oil, which was pulverized with isopropyl ether to give Z-(L)-Boc-(D)-mesoDAP-(D)-NHNHBoc-(L)-NHCH$_2$CH$_2$OH (2) (5.76 g).

IR (Nujol): 3280, 1710, 1690, 1675, 1745 cm$^{-1}$.

NMR (CDCl$_3$): δ1.42 (18H, s), 1.4–2.0 (6H, m), 3.2–3.7 (5H, m), 4.0–4.4 (2H, m), 5.06 (2H, s), 5.72 (1H, d, J=8 Hz), 6.26 (1H, d, J=8 Hz), 7.30 (5H, s), 7.40 (1H, br s), 9.08 (1H, br s).

Preparation 4

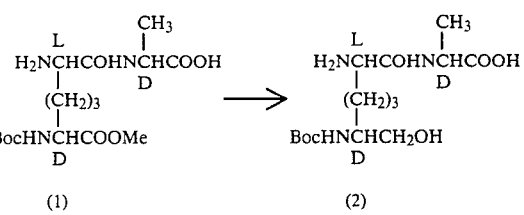

To a cooled solution of sodium borohydride (13.57 g) in water (140 ml) was added a solution of Boc-(D)-mesoDAP-(D)-OMe-(L)-D-AlaOH (1)(7.2 g) in water (100 ml) during a period of 30 minutes and the mixture was stirred for 1 hour at room temperature. The reaction mixture was adjust to pH 3 with 10% hydrochloric acid under ice-bath cooling and put on a column of a macroporous non-ionic resin, HP-20 (200 ml). The column was washed with water and eluted with 60% aqueous methanol. The eluate was concentrated and the residue was crystallized with ether to give Boc-(D)-(L-α-amino-D-ε-amino-ε hydroxymethyl)hexanoyl-(L)-D-AlaOH (2) (5.24 g). mp. 82°–85° C. (dec.)

IR (Nujol): 3250, 1670 cm$^{-1}$.

NMR (D$_2$O): δ1.48 (9H, s), 1.1–2.3 (9H, m), 3.4–4.1 (4H, m), 4.22 (1H, q, J=7 Hz).

EXAMPLE 1

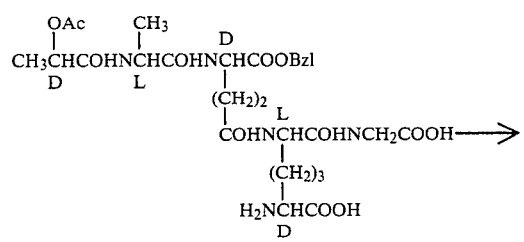

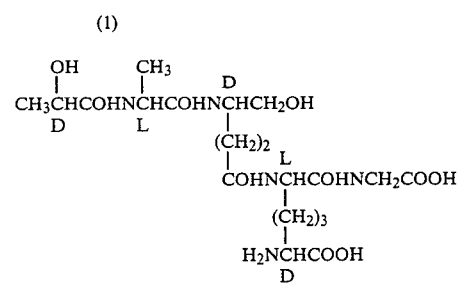

To a solution of sodium borohydride (2.39 g) in water (20 ml) was added a solution of D-Lac(OAc)-L-Ala-γ-

D-Glu(α-OBzl)-(L)-mesoDAP-(L)-GlyOH (1)(2.06 g) in 1.5% aqueous sodium bicarbonate (200 ml) during 5 minutes at room temperature. After stirring for 4 hours at the same temperature, the reaction mixture was acidified to pH 3 with 10% hydrochloric acid and concentrated to about 40 ml. The concentrate was put on a column of an activated charcoal (140 ml) and, after washing with water, eluted with 50% aqueous methanol. The eluate was concentrated and the residue was dissolved in a small amount of water and put on a column of a macroporous non-ionic adsorption resin, HP-20 (240 ml) and eluted with water. The eluate was concentrated and lyophilized to give D-Lac-L-Ala-γ-D-(α-amino-α-hydroxymethyl)butyryl-(L)-mesoDAP-(L)-GlyOH (2)(107 g).

$[\alpha]_D - 24.2°$ C. (C=1.0, H$_2$O).

IR (Nujol): 3230, 1710, 1630 cm$^{-1}$.

NMR (D$_2$O): δ1.26 (3H, d, J=7 Hz), 1.20–2.16 (8H, m), 1.43 (3H, d, J=7 Hz), 2.34 (2H, t, J=7 Hz), 3.5–3.7 (2H, m), 3.79 (1H, t, J=6 Hz), 3.96 (2H, s), 4.1–4.5 (4H, m).

EXAMPLE 2

(1) Step 1

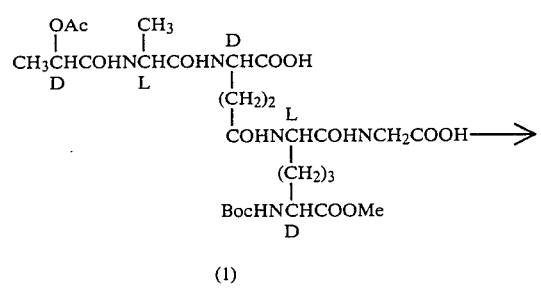

(1)

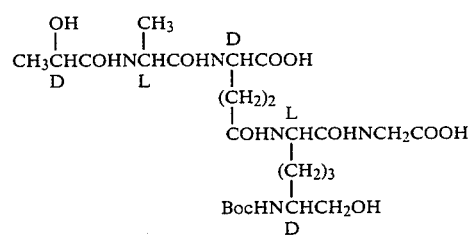

(2)

D-Lac-L-Ala-γ-D-Glu(α-OH)-(L)-Boc-(D)-(L-α-amino-D-ε-amino-ε-hydroxymethyl)hexanoyl-(L)-GlyOH (2) was prepared in a similar manner to the Example 1.

NMR (D$_2$O): δ1.42 (9H, s), 1.1–2.6 (16H, m), 3.2–3.7 (2H, m), 3.93 (2H, s), 4.0–4.4 (5H, m).

(2) Step 2

Compound (2) ⟶

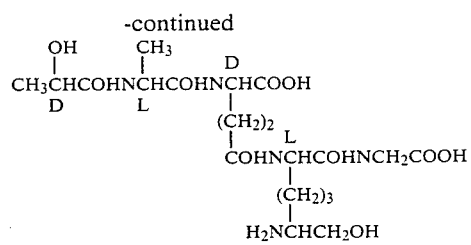

(3)

D-Lac-L-ALa-γ-D-GLu(α-OH)-(L)-Boc-(D)-(L-α-amino-D-ε-amino-ε-hydroxymethyl)hexanoyl-(L)-GlyOH (2)(0.74 g) was added to trifluoroacetic acid (10 ml) and the mixture was stirred for 15 minutes at room temperature. After concentration of the reaction mixture, the residue was dissolved in water (20 ml) and neutralized to pH 3 with 2.5N sodium hydroxide. This solution was put on a column of an activated charcoal (30 ml) and, after washing with water, eluted with 50% aqueous methanol. The eluate was concentrated and the residue was dissolved in a small amount of water and put on a column of a macroporous non-ionic adsorption resin, HP-20 (90 ml). Elution with water and evaporation of the eluate, followed by lyophilization, gave D-Lac-L-Ala-γ-D-Glu(α-OH)-(L)-(L-α-amino-D-ε-amino-ε-hydroxymethyl)hexanoyl-(L)-GlyOH (3) (0.46 g).

$[\alpha]_D = 32.3°$ (C=0.2, H$_2$O).

IR (KBr): 3360, 1650, 1530 cm$^{-1}$.

NMR (D$_2$O): δ 1.1–2.5 (10H, m), 1.34 (3H, d, J=7 Hz), 1.45 (3H, d, J=7 Hz), 3.30 (1H, m), 3.50 (2H, m), 3.87 (2H, s), 4.1–4.4 (4H, m).

EXAMPLE 3

(1) Step 1

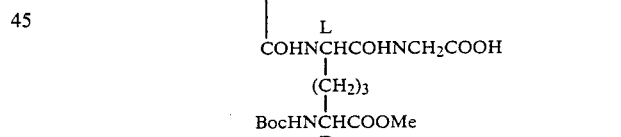

(1)

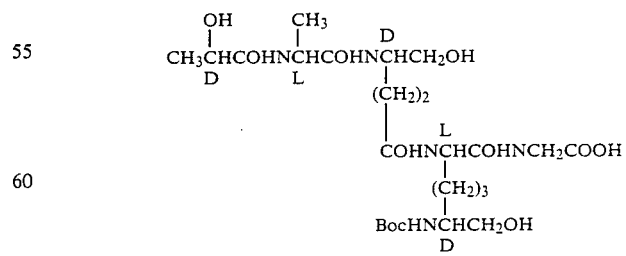

(2)

D-Lac-L-Ala-γ-D-(α-amino-α-hydroxymethyl)butyryl-(L)-Boc-(D)-(L-α-amino-D-ε-amino-ε-hydroxymethyl)hexanoyl-(L)-GlyOH (2) was prepared in a similar manner to the Example 1.

IR (KBr): 3360, 2950, 1650, 1530 cm$^{-1}$.

NMR (D$_2$O): δ 1.3–2.7 (16H, m), 1.45 (9H, s), 3.5–3.7 (4H, m), 3.80 (2H, s), 4.1–4.5 (5H, m).

(2) Step 2

Compound (2) ⟶

$$\begin{array}{c}
\text{OH} \quad\quad \text{CH}_3 \quad\quad \text{D} \\
| \quad\quad\quad | \quad\quad\quad | \\
\text{CH}_3\text{CHCOHNCHCOHNCHCH}_2\text{OH} \\
\text{D} \quad\quad \text{L} \quad\quad\quad | \\
\quad\quad\quad\quad\quad\quad (\text{CH}_2)_2 \\
\quad\quad\quad\quad\quad\quad | \quad\quad \text{L} \\
\quad\quad\quad\quad\quad\quad \text{COHNCHCOHNCH}_2\text{COOH} \\
\quad\quad\quad\quad\quad\quad\quad\quad\quad | \\
\quad\quad\quad\quad\quad\quad\quad\quad\quad (\text{CH}_2)_3 \\
\quad\quad\quad\quad\quad\quad\quad\quad\quad | \\
\quad\quad\quad\quad\quad\quad\quad\quad\quad \text{H}_2\text{NCHCH}_2\text{OH} \\
\quad\quad\quad\quad\quad\quad\quad\quad\quad\quad \text{D}
\end{array}$$

(3)

D-Lac-L-Ala-γ-D-(α-amino-α-hydroxymethyl)-butyryl(L)-(L-α-amino-D-ε-amino-ε-hydroxymethyl)-hexanoyl-(L)-GlyOH (3) was prepared in a similar manner to Step 2 of Example 2.

[α]$_D$ −27.6° (C=0.2, H$_2$O).

IR (KBr): 3340, 2950, 1645, 1545 cm$^{-1}$.

NMR (D$_2$O): δ 1.1–2.1 (8H, m), 1.34 (3H, d, J=7 Hz), 1.45 (3H, d, J=7 Hz), 2.34 (2H, t, J=7 Hz), 3.2–4.0 (5H, m), 3.77 (2H, s), 4.1–4.4 (4H, m).

EXAMPLE 4

(1) Step 1

$$\begin{array}{c}
\quad\quad\quad\quad \text{CH}_3 \quad \text{D} \\
\quad\quad\quad\quad\quad | \quad\quad | \\
\text{CH}_3(\text{CH}_2)_{16}\text{COHNCHCOHNCHCOOBzl} + \\
\quad\quad\quad\quad\quad\quad \text{L} \quad\quad | \\
\quad\quad\quad\quad\quad\quad\quad\quad (\text{CH}_2)_2 \\
\quad\quad\quad\quad\quad\quad\quad\quad | \\
\quad\quad\quad\quad\quad\quad\quad\quad \text{COOSu}
\end{array}$$

(1)

$$\begin{array}{c}
\quad\quad\quad\quad\quad\quad \text{CH}_3 \\
\text{L} \quad\quad\quad\quad\quad | \\
\text{H}_2\text{NCHCOHNCHCOOH} \longrightarrow \\
| \quad\quad\quad\quad\quad \text{D} \\
(\text{CH}_2)_3 \\
| \\
\text{BocHNCHCH}_2\text{OH} \\
\text{D}
\end{array}$$

(2)

$$\begin{array}{c}
\quad\quad\quad\quad\quad \text{CH}_3 \quad\quad \text{D} \\
\quad\quad\quad\quad\quad\quad | \quad\quad\quad | \\
\text{CH}_3(\text{CH}_2)_{16}\text{COHNCHCOHNCHCOOBzl} \\
\quad\quad\quad\quad\quad\quad\quad \text{L} \quad\quad | \\
\quad\quad\quad\quad\quad\quad\quad\quad\quad (\text{CH}_2)_2 \\
\quad\quad\quad\quad\quad\quad\quad\quad\quad | \quad\quad \text{CH}_3 \\
\quad\quad\quad\quad\quad\quad\quad\quad\quad | \quad\quad\quad \text{L} \quad | \\
\quad\quad\quad\quad\quad\quad\quad\quad\quad \text{COHNCHCOHNCHCOOH} \\
\quad\quad\quad\quad\quad\quad\quad\quad\quad\quad\quad | \\
\quad\quad\quad\quad\quad\quad\quad\quad\quad\quad\quad (\text{CH}_2)_3 \\
\quad\quad\quad\quad\quad\quad\quad\quad\quad\quad\quad | \\
\quad\quad\quad\quad\quad\quad\quad\quad\quad\quad\quad \text{BocHNCHCH}_2\text{OH} \\
\quad\quad\quad\quad\quad\quad\quad\quad\quad\quad\quad\quad \text{D}
\end{array}$$

(3)

To a solution of Boc-(D)-(D-ε-amino-ε-hydroxymethyl-L-α-amino)hexanoyl-(L)-D-AlaOH (2) (694 mg) and triethylamine (240 mg) in methylene chloride (20 ml) was added stearoyl-L-Ala-D-Glu(OSu)OBzl (1)(1.34 g) and the mixture was kept for 7 hours at room temperature. After evaporation of the solvent, water (30 ml) and 1N hydrochloric acid (3 ml) were added to the residue. The precipitate was filtered and washed successively with water and hot isopropyl ether to give stearoyl-L-Ala-γ-D-Glu(α-OBzl)-(L)-Boc-(D)-(L-ε-amino-ε-hydroxymethyl)hexanoyl-(L)-D-AlaOH (3)(1.67 g). mp. 141°–143° C.

IR (Nujol): 3300, 1740, 1650 cm$^{-1}$.

NMR (CDCl$_3$-CD$_3$OD): δ 0.89 (3H, m), 1.1–2.5 (57H, m), 3.55 (1H, m), 5.20 (2H, s), 7.36 (5H, s).

(2) Step 2

Compound (3) ⟶

$$\begin{array}{c}
\quad\quad\quad\quad\quad \text{CH}_3 \quad\quad \text{D} \\
\quad\quad\quad\quad\quad\quad | \quad\quad\quad | \\
\text{CH}_3(\text{CH}_2)_{16}\text{COHNCHCOHNCHCOOH} \\
\quad\quad\quad\quad\quad\quad\quad \text{L} \quad\quad | \\
\quad\quad\quad\quad\quad\quad\quad\quad\quad (\text{CH}_2)_2 \\
\quad\quad\quad\quad\quad\quad\quad\quad\quad | \quad\quad\quad\quad \text{CH}_3 \\
\quad\quad\quad\quad\quad\quad\quad\quad\quad | \quad\quad\quad \text{L} \quad | \\
\quad\quad\quad\quad\quad\quad\quad\quad\quad \text{COHNCHCOHNCHCOOH} \\
\quad\quad\quad\quad\quad\quad\quad\quad\quad\quad\quad | \quad\quad\quad \text{D} \\
\quad\quad\quad\quad\quad\quad\quad\quad\quad\quad\quad (\text{CH}_2)_3 \\
\quad\quad\quad\quad\quad\quad\quad\quad\quad\quad\quad | \\
\quad\quad\quad\quad\quad\quad\quad\quad\quad\quad\quad \text{HCl.H}_2\text{NCHCH}_2\text{OH} \\
\quad\quad\quad\quad\quad\quad\quad\quad\quad\quad\quad\quad \text{D}
\end{array}$$

(4)

A solution of stearoyl-L-Ala-γ-D-Glu(α-OBzl)-(L)-Boc-(D)-(D-ε-amino-ε-hydroxymethyl)hexanoyl-(L)-D-AlaOH (3)(1.50 g) in acetic acid (40 ml) was hydrogenated over 10% palladium-charcoal (400 mg) under an atmospheric pressure of hydrogen. After removal of the catalyst, acetic acid (10 ml) saturated with hydrogen chloride was added to the filtrate and the mixture was kept for 5 hours at room temperature. After evaporation of the solvent, a small amount of toluene was added to the residue and the mixture was evaporated to leave a crystalline mass, which was washed with isopropyl ether to give stearoyl-L-Ala-γ-D-Glu(α-OH)-(L)-(D-ε-amino-ε-hydroxymethyl-L-α-amino)hexanoyl-(L)-D-AlaOH hydrochloride (4)(1.16 g).

mp. 148°–153° C.

IR (Nujol): 3300, 1725, 1625 cm$^{-1}$.

NMR (CDCl$_3$-CD$_3$OD): δ 0.91 (3H, m), 1.1–2.6 (48H, m).

EXAMPLE 5

(1) Step 1

$$\begin{array}{c}
\quad\quad\quad\quad\quad\quad\quad \text{D} \\
\quad\quad\quad\quad\quad\quad\quad | \\
\text{CH}_3(\text{CH}_2)_5\text{COHNCHCOOBzl} \\
\quad\quad\quad\quad\quad\quad\quad | \\
\quad\quad\quad\quad\quad\quad\quad (\text{CH}_2)_2 \quad + \\
\quad\quad\quad\quad\quad\quad\quad | \\
\quad\quad\quad\quad\quad\quad\quad \text{COSu}
\end{array}$$

(1)

$$\begin{array}{c}
\quad\quad\quad\quad\quad\quad \text{CH}_3 \\
\text{L} \quad\quad\quad\quad\quad | \\
\text{H}_2\text{NCHCOHNCHCOOH} \\
| \quad\quad\quad\quad\quad \text{D} \\
(\text{CH}_2)_3 \quad\quad\quad\quad \longrightarrow \\
| \\
\text{BocHNCHCH}_2\text{OH} \\
\text{D}
\end{array}$$

(2)

-continued

```
            D
CH3(CH2)5COHNCHCOOBzl
            |
          (CH2)2
            |          CH3
        L   |      |
        COHNCHCOHNCHCOOH
            |          D
          (CH2)3
            |
        BocHNCHCH2OH
            D
```

(3)

To a solution of Boc-(D)-(D-ϵ-amino-ϵ-hydroxymethyl-L-α-amino)hexanoyl-(L)-D-AlaOH (2)(1.13 g) and triethylamine (0.36 g) in methylene chloride (20 ml) was added n-heptanoyl-D-Glu(OSu)OBzl (1)(1.34 g). After keeping at room temperature for 16 hours, the mixture was concentrated and, to the residue, a mixture of 1N hydrochloric acid (40 ml) and water (20 ml) was added. The resulting precipitate was collected and washed with water to give white crystals, which was then washed with hot isopropyl ether to give n-heptanoyl-γ-D-Glu(α-OBzl)-(L)-Boc-(D)-(D-ϵ-amino-ϵ-hydroxymethyl-L-α-amino)hexanoyl-(L)-D-AlaOH (3)(1.74 g). mp. 155°–162° C.

IR (Nujol): 3300, 1735, 1685, 1635 cm$^{-1}$.

NMR (CD$_3$OD): δ 0.86 (3H, m), 1.13–2.44 (32H, m), 3.40 (3H, m), 4.20–4.52 (3H, m), 5.12 (2H, s), 7.31 (5H, s).

(2) Step 2

Compound (3) ⟶

```
            D
CH3(CH2)5COHNCHCOOH
            |
          (CH2)2
            |          CH3
        L   |      |
        COHNCHCOHNCHCOOH
            |          D
          (CH2)3
            |
        H2NCHCH2OH
            D
```

(4)

A solution of n-heptanoyl-γ-D-Glu(α-OBzl)-(L)-Boc-(D)-(D-ϵ-amino-ϵ-hydroxymethyl-L-α-amino)hexanoyl-(L)-D-AlaOH (3)(1.64 g) in acetic acid (30 ml) was hydrogenated over 10% palladium charcoal (0.30 g) under an atmospheric pressure of hydrogen. After removal of the catalyst by filtration, acetic acid (5 ml) saturated with hydrogen chloride was added to the filtrate. The mixture was stirred at room temperature for 2 hours and concentrated to give an oily residue, which was applied to a column of HP-20 (30 ml).

The fractions eluted with a mixture of chloroforum and methanol (7:3) were collected and evaporated. Lyophilization gave n-heptanoyl-γ-D-Glu(α-OH)-(L)-(D-ϵ-amino-ϵ-hydroxymethyl-L-α-amino)hexanoyl-(L)-D-AlaOH (4)(0.60 g).

mp. 121° C. (dec.).

[α]$_D$ −24.0 (C. 0.2, MeOH).

IR (Nujol): 3280, 1720, 1640 cm$^{-1}$.

NMR (D$_2$O): δ 0.86 (3H, m), 1.05–2.65 (23H, m), 3.25–3.90 (3H, m), 3.95–4.50 (3H, m).

EXAMPLE 6

(1) Step 1

```
     OAc     CH3
      |       |       D
CH3CHCOHNCHCOHNCHCOOBzl +
      D      L       |
                  (CH2)2
                     |
                   COOH
```

(1)

```
            L
    H2NCHCOHNCH2CH2OH
            |
          (CH2)3
            |
        BocHNCHCOHNNHBoc
            D
```

(2)

```
     OAc     CH3
      |       |       D
CH3CHCOHNCHCOHNCHCOOBzl
      D      L       |
                  (CH2)2
                     |       L
                   COHNCHCOHNCH2CH2OH
                     |
                  (CH2)3
                     |
                 BocHNCHCOHNNHBoc
                     D
```

(3)

D-Lac(OAc)-L-Ala-γ-D-Glu(α-OBzl)-(L)-Boc-(D)-mesoDAP-(D)-NHNHBoc-(L)-HNCH$_2$CH$_2$OH (3) was prepared in a similar manner to step 1 of Example 4.

IR (Nujol): 3250, 1710, 1660, 1630 cm$^{-1}$.

NMR (CD$_3$OD): δ 1.2–1.9 (30H, m), 2.07 (3H, s), 2.0–2.4 (4H, m), 3.4–3.7 (4H, m), 3.9–5.0 (5H, m), 5.18 (2H, s), 7.37 (5H, s).

(2) Step 2

Compound (3) ⟶

```
     OAc     CH3
      |       |       D
CH3CHCOHNCHCOHNCHCOOBzl
      D      L       |
                  (CH2)2
                     |       L
                   COHNCHCOHNCH2CH2OH
                     |
                  (CH2)3
                     |
                  H2NCHCOOH
                     D
```

(4)

D-Lac(OAc)-L-Ala-γ-D-Glu(α-OBzl)-(L)-Boc-(D)-mesoDAP-(D)-NHNHBoc-(L)-NHCH$_2$CH$_2$OH (3)(2.0 g) was added to trifluoroacetic acid (20 ml) and the mixture was stirred for 1 hour at room temperature. After evaporation of trifluoroacetic acid, the residue was washed with ether and dissolved in a mixture of water (20 ml), 1N hydrochloric acid (2.5 ml), and dioxane (10 ml). This solution was cooled to 0° C. and bromine (0.30 g) was added. After stirring for 5 minutes at the same temperature, the reaction mixture was treated with aqueous sodium sulfate until the brown color was disappeared. Dioxane was evaporated and the resulting aqueous solution was adjusted to pH 3 and put on a column of a macroporous non-ionic adsorption resin, HP-20 (50 ml). The column was washed with water and eluted with 80% aqueous methanol. The eluate was evaporated to give a crystalline solid, which was washed with ether to give D-Lac(OAc)-L-Ala-γ-D-Glu(α-OBzl)-(L)-mesoDAP-(L)-NHCH₂CH₂OH (4)(1.08 g).

IR (Nujol): 3260, 1720, 1635 cm⁻¹.

NMR (CD₃OD): δ 1.39 (3H, d, J=7 Hz), 1.46 (3H, d, J=7 Hz), 2.11 (3H, s), 1.5–2.4 (10H, m), 3.5–3.7 (4H, m), 4.2–5.1 (5H, m), 5.16 (2H, s), 7.34 (5H, s).

(3) Step 3

Compound (4) ⟶

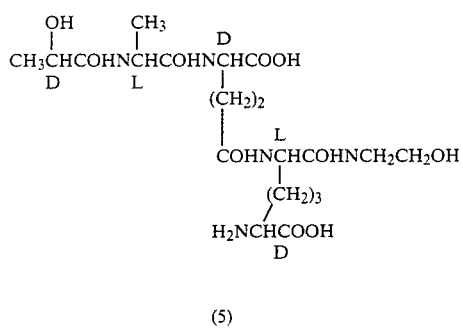

(5)

To a solution of D-Lac-(OAc)-L-Ala-γ-D-Glu(α-OBzl)-(L)-mesoDAP-(L)-NHCH₂CH₂OH (4)(1.77 g) in 50% aqueous methanol (36 ml) was added 1N sodium hydroxide (8.4 ml) and the mixture was stirred for 2 hours at room temperature. After evaporation of methanol, the resulting aqueous solution was adjusted to pH 3 with 5% hydrochloric acid and put on a column of an activated charcoal (60 ml). The column was washed with water and eluted with 60% aqueous methanol. The eluate was concentrated and lyophilized to give D-Lac-L-Ala-γ-D-Glu(α-OH)-(L)-mesoDAP-(L)-NHCH₂CH₂OH (5)(0.90 g).

IR (Nujol): 3300, 1730, 1640 cm⁻¹.

NMR (D₂O): δ1.35 (3H, d, J=7 Hz), 1.42 (3H, d, J=7 Hz), 1.5–2.4 (10H, m), 3.32 (2H, t, J=6 Hz), 3.64 (2H, t, J=6 Hz), 3.76 (1H, t, J=6 Hz), 4.1–4.5 (5H, m).

EXAMPLE 7

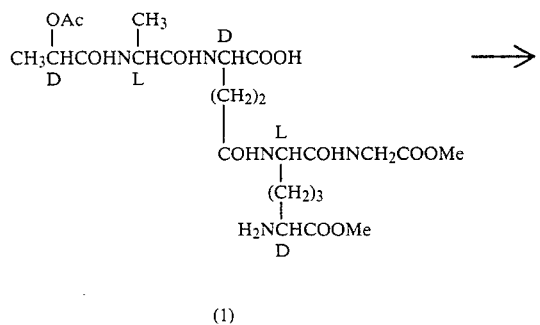

(1)

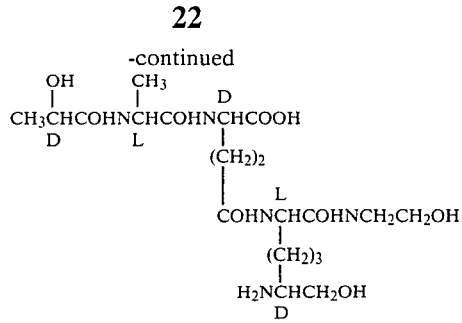

(2)

D-Lac-L-Ala-γ-D-Glu(α-OH)-(L)-(L-α-amino-D-ε-amino-ε-hydroxymethyl)hexanoyl-(L)-NHCH₂CH₂OH (2) was prepared in a similar manner to the Example 1.

[α]_D −29.3° (C=0.145, H₂O).

IR (KBr): 3250, 1630, 1520 cm⁻¹.

NMR (D₂O): δ 1.2–2.5 (10H, m), 1.36 (3H, d, J=7 Hz), 1.43 (3H, d, J=7 Hz), 3.2–3.9 (7H, m), 4.2–4.5 (4H, m).

EXAMPLE 8

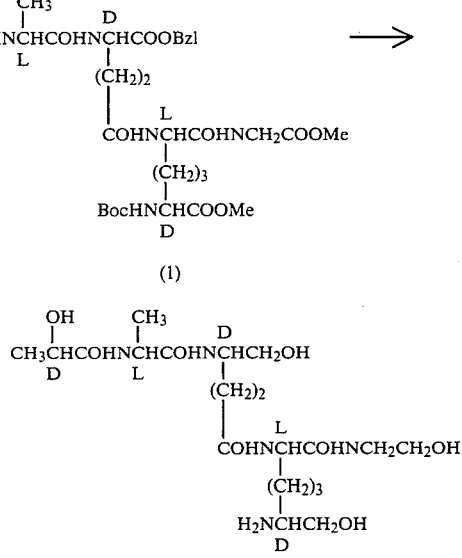

D-Lac(OAc)-L-Ala-γ-D-Glu(α-OBzl)-(L)-Boc-(D)-mesoDAP-(D)-OMe-(L)-GlyOMe (1)(1.95 g) was added to trifluoroacetic acid (20 ml) and the mixture was stirred for 20 minutes at room temperature. After evaporation of trifluoroacetic acid, the residue was dissolved in water (50 ml) and added into a cooled solution of sodium borohydride (5.67 g) in water (50 ml). After stirring for 1.5 hours at room temperature, the mixture was acidified to pH 4 with 10% hydrochloric acid and concentrated to about 50 ml. The concentrate was put on a column of an activated charcoal (60 ml) and, after washing with water, eluted with 60% aqueous methanol. The eluate was concentrated and the residue was dissolved in a small amount of water and put on a column of macroporous non-ionic adsorption resin, HP-20 (50 ml). The column was eluted with water and eluate was concentrated and lyophilized to give D-Lac-L-Ala-γ-D-(α-amino-α-hydroxymethyl)butyryl-(L)-(L-α-amino-D-ε-amino-ε-hydroxymethyl)hex-anoyl-(L)-NHCH₂CH₂OH (2) (0.73 g).

[α]$_D$ −17.7° (C=0.357, H₂O).

IR (KBr): 3300, 1630, 1530 cm$^{-1}$.

NMR (D₂O): δ 1.39 (3H, d, J=7 Hz), 1.46 (3H, d, J=7 Hz), 1.1–2.1 (8H, m), 2.36 (2H, t, J=7 Hz), 3.37 (2H, t, J=6 Hz), 3.5–4.1 (7H, m), 4.1–4.5 (4H, m).

EXAMPLE 9

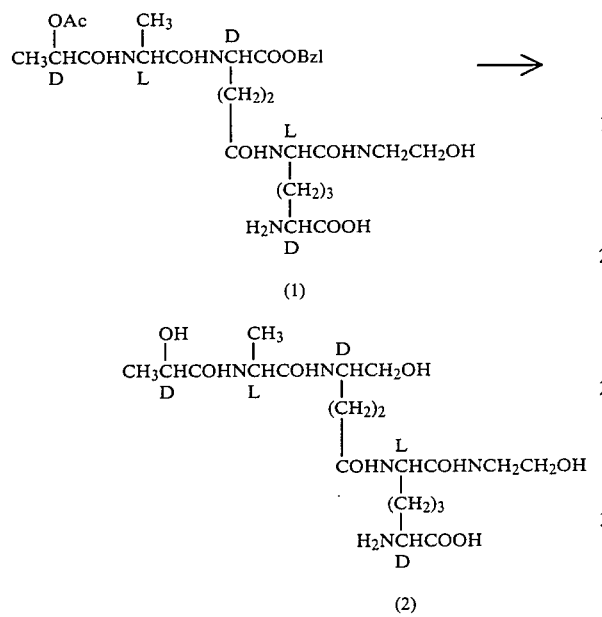

D-Lac-L-Ala-γ-D-(α-amino-α-hydroxymethyl)-butyryl(L)-mesoDAP-(L)-NHCH₂CH₂OH (2) was prepared in a similar manner to the Example 1.

[α]$_D$ −21.0° (C=1.0, H₂O).

IR (KBr): 3350, 1635, 1530 cm$^{-1}$.

NMR (D₂O): δ 1.40 (3H, d, J=7 Hz), 1.45 (3H, d, J=6 Hz), 1.2–2.1 (8H, m), 2.33 (2H, t, J=7 Hz), 3.36 (2H, t, J=6 Hz), 3.5–4.0 (5H, m), 4.1–4.5 (4H, m).

Preparation 5

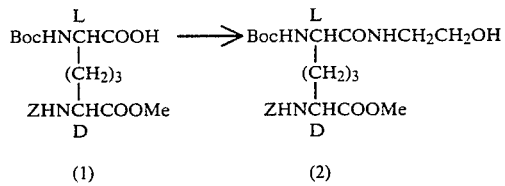

Isobutyl chloroformate was added to a mixture of Boc-(L)-Z-(D)-mesoDAP-(D)-OMe (1) (5.13 g) and N-methylmorpholine (1.18 g) in methylene dichloride (100 ml) at −10° to −15° C. The mixture was stirred for 30 minutes at the same temperature and then cooled to −30° to −40° C. To the mixture was added a solution of ethanolamine (0.72 g) in methylene chloride (6 ml) and the resulting mixture was stirred for 2 hours at −10° to −15° C. After evaporation of the solvent, the residue was dissolved in ethyl acetate (150 ml). Ethyl acetate layer was washed subsequently with 2.5% hydrochloric acid (50 ml), 1% hydrochloric acid (50 ml), water (50 ml), 2.5% sodium bicarbonate (50 ml) and water (50 ml), and then dried over magnesium sulfate. The solvent was removed under a reduced pressure to give Boc-(L)-Z-(D)-mesoDAP-(L)-NH(CH₂)₂OH-(D)-OMe (2) (5.39 g).

NMR (CDCl₃) δ: 1.40 (9H, s), 1.4 to 2.0 (6H, m), 3.2 to 3.6 (4H, m), 3.73 (3H, s), 3.9 to 4.5 (2H, m), 5.12 (2H, s), 7.35 (5H, s).

EXAMPLE 10

(1) step 1

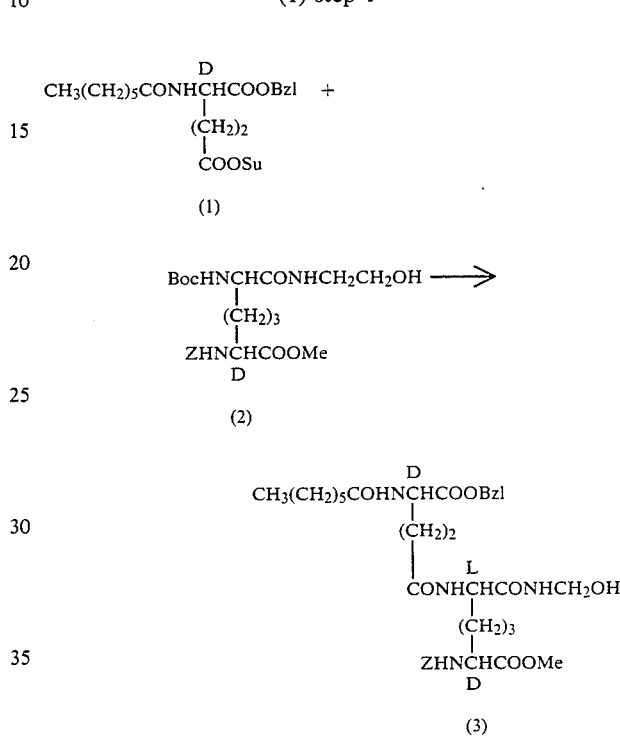

Boc-(L)-Z-(D)-mesoDAP-(L)-NH(CH₂)₂OH-(D)-OMe (2) (420 mg) was dissolved in trifluoroacetic acid (4 ml) and the mixture was stirred for 30 minutes at room temperature. After removal of trifluoroacetic acid under reduced pressure, the residue was dissolved in 50% aqueous dioxane (20 ml) The mixture was adjusted to PH 8 with triethylamine and a solution of heptanoyl-D-Glu(OSu)OBzl (1) (0.39 g) in dioxane (4 ml) was added. The reaction mixture was stirred for 1.5 hours at room temperature. After evaporation of dioxane, the resulting aqueous solution was acidified to PH 3 with 5% hydrochloric acid. The precipitated crystalline solid was collected by filtration, washed with water to give heptanoyl-r-D-Glu(α-OBzl)-(L)-Z-(D)-mesoDAP-(L)-NH(CH₂)₂OH-(D)-OMe (3) (540 mg).

NMR (CD₃OD), δ: 0.88 (3H, t, J=6 Hz), 1.0 to 2.4 (20H, m), 3.2 to 3.6 (4H, m), 3.66 (3H, s), 4.0 to 4.6 (3H, m), 5.05 (2H, s), 5.12 (2H, s), 7.32 (10H, m).

(2) step 2

Compound (3) ⟶

-continued

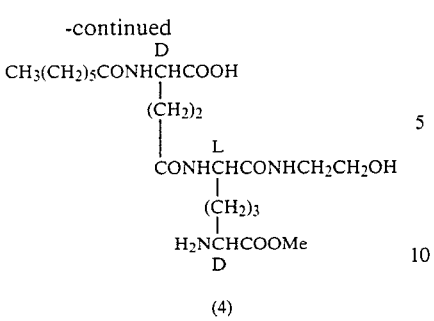

(4)

A solution of heptanoyl-r-D-Glu(α-OBzl)-(L)-Z-(D)-mesoDAP-(L)-NH(CH₂)₂OH-(D)-OMe (3) (2.0 g) in mixture of methanol (65 ml) and water (5 ml) was hydrogenated over 10% palladium-charcoal (0.6 g) for 3.5 hours. After removal of the catalyst by filtration, the filtrate was concentrated under reduced pressure. The residue was dissolved in water (40 ml) and this solution was put on a column packed with HP-20 (40 ml). This column was washed with water and eluted with 30% aqueous methanol (500 ml). The eluate was concentrated to about 10 ml and lyophilised to give heptanoyl-r-D-Glu(α-OH)-(L)-mesoDAP-(L)-NH(CH₂)₂OH-(D)-OMe (4) (0.87 g).

NMR (D₂O, δ): 0.87 (3H, t, J=5 Hz), 1.0–2.5 (20H, m), 3.2–3.7 (4H, m), 3.87 (3H, s), 4.0–4.4 (3H, m),

IR(Nujol): 3270, 1750, 1640, 1540, 1225, 1170 1065 cm⁻¹.

(3) step 3

Compound (3) ⟶

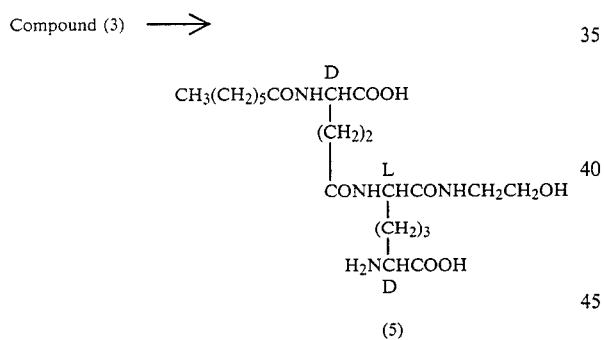

(5)

To solution of heptanoyl -r-D-Glu(α-OBzl)-(L)-Z-(D)-mesoDAP-(L)-NH(CH₂)₂OH-(D)-OMe (3) (0.356 g) in a mixture of methanol (10 ml) and water (5 ml) was added 1N-sodium hydroxide (1 ml) and the mixture was stirred for 6 hours at room temperature. After evaporation of methanol, the resulting aqueous solution was acidified to PH 2 with 5% hydrochloric acid and extracted with ethyl acetate (25 ml). The organic layer was washed with water (10 ml), dried over magnesium sulfate and evaporated to dryness under reduced pressure. The residue was dissolved in methanol (10 ml) and this solution was hydrogenated over 10% palladium charcoal (0.1 g) for 3.5 hours. After removal of the catalyst by filtration, the filtrate was concentrated under reduced pressure. The residue was chromatographed on HP-20 (9 ml) with 30% aqueous methanol to give heptanoyl -r-D-Glu(α-OH)-(L)-mesoDAP-(L)-NH(CH₂)₂OH (5) (170 mg).

NMR (D₂O, δ): 0.83 (3H, t, J=5 Hz), 1.0–2.5 (20H, m), 3.2–3.6 (4H, m), 3.73 (1H, t, J=6 Hz), 4.1–4.4 (2H, m).

IR (Nujol): 3370, 1720, 1640, 1540, 1224, 1130 1065⁻¹.

We claim:

1. A compound of the formula or its pharmaceutically acceptable salt:

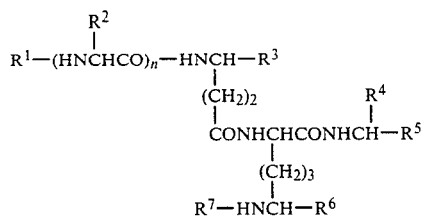

wherein
R¹ is heptanoyl, stearoyl, 2-hyroxypropionyl or 2-acetoxypropionyl,
R² is hydrogen or methyl,
R³ is carboxy, benzyloxycarbonyl or hydroxymethyl,
R⁴ is hydrogen or methyl,
R⁵ is carboxy or hydroxymethyl,
R⁶ is carboxy, methoxycarbonyl, 3-t-butoxycarbonylcarbazoyl or hydroxymethyl,
R⁷ is hydrogen, 3-t-butoxycarbonyl or benzyloxycarbonyl, and
n is an integer 0 or 1, with the proviso that at least one of R³, R⁵ and R⁶ is hydroxymethyl.

2. A compound of the formula or its pharmaceutically acceptable salt:

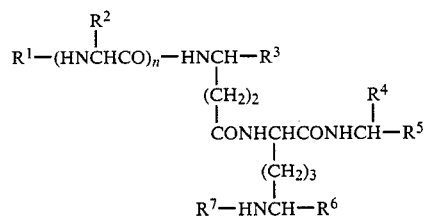

wherein
R¹ is heptanoyl, stearoyl, 2-hydroxypropionyl or 2-acetoxypropionyl,
R² is hydrogen or methyl,
R³ is carboxy, benzyloxycarbonyl or hydroxymethyl,
R⁴ is hydrogen or methyl,
R⁵ is carboxy or hydroxymethyl,
R⁶ is carboxy, methoxycarbonyl, 3-t-butoxycarbonylcarbazoyl or hydroxymethyl,
R⁷ is hydrogen, 3-t-butoxycarbonyl or benzyloxycarbonyl, and
n is an integer 0 or 1, with the proviso that when each of R³ and R⁶ is not simultaneously hydroxymethyl, then R⁵ is hydroxymethyl.

3. The compound according to claim 1, wherein R¹ is 2-hydroxypropionyl, R² is methyl, R³ is hydroxymethyl, R⁴ is hydrogen, R⁵ is carboxy, R⁶ is carboxy, R⁷ is hydrogen, and n is 1.

4. The compound according to claim 1, wherein R¹ is 2-hydroxypropionyl, R² is methyl, R³ is carboxy, R⁴ is hydrogen, R⁵ is carboxy, R⁶ is hydroxymethyl, R⁷ is hydrogen, and n is 1.

5. The compound according to claim 2, wherein R¹ is 2-hydroxypropionyl, R² is methyl, R³ is hydroxymethyl, R⁴ is hydrogen, R⁵ is carboxy, R⁶ is hydroxymethyl, R⁷ is hydrogen, and n is 1.

6. The compound according to claim 1, wherein $R^1$ is heptanoyl, $R^3$ is carboxy, $R^4$ is methyl, $R^5$ is carboxy, $R^6$ is hydroxymethyl, $R^7$ is hydrogen, and n is 0.

7. A process for preparation of a compound of the formula or its pharmaceutically acceptable salt:

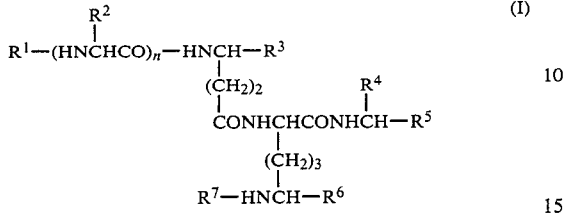

wherein
- $R^1$ is hydrogen or acyl,
- $R^2$ and $R^4$ are each hydrogen or lower alkyl,
- $R^3$ and $R^6$ are each carboxy, protected carboxy, carbamoyl or hydroxymethyl,
- $R^5$ is hydrogen, carboxy, protected carboxy, carbamoyl, carboxy or protected carboxy(lower)alkyl, or hydroxy(lower)alkyl,
- $R^7$ is hydrogen or an amino protective group, and
- n is an integer 0 or 1, with proviso that in the restricted case that each of $R^3$ and $R^6$ is not simultaneously hydroxymethyl, $R^5$ should be always hydroxy(lower)alkyl, which comprises (1) reacting a compound of the formula or its salt:

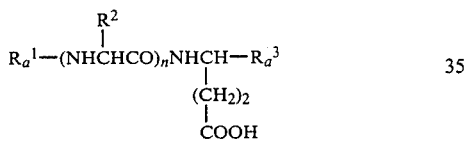

with a compound of the formula or it or its salt:

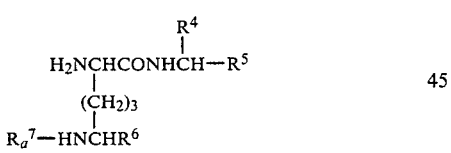

to give a compound of the formula or its salt:

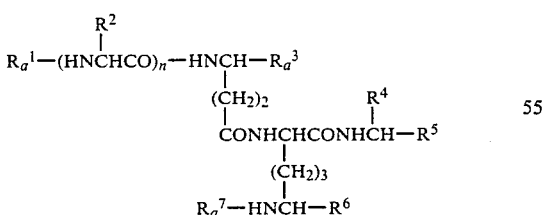

in the above formulae, $R_a^1$ is acyl, $R_a^3$ is protected carboxy, carbamoyl, hydroxymethyl, $R_a^7$ is an amino protective group, and $R^2$, $R^4$, $R^5$, $R^6$ and n are each as defined above, with proviso that in the restricted case that each of $R_a^3$ and $R^6$ is not simultaneously hydroxymethyl, $R^5$ should be hydroxy(lower)alkyl, or (2) reducing a compound of the formula or its salt:

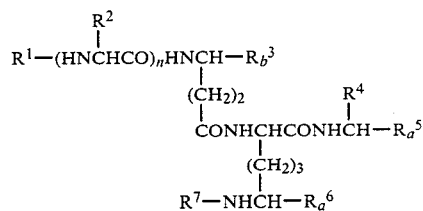

wherein $R_b^3$ and $R_a^6$ are each carboxy, protected carboxy excepting esterified carboxy, esterified carboxy, carbamoyl or hydroxymethyl, $R_a^5$ is hydrogen, carboxy, protected carboxy excepting esterified carboxy, esterified carboxy, carbamoyl, carboxy(lower)alkyl, protected carboxy excepting esterified carboxy(lower)alkyl, esterified carboxy(lower)alkyl or hydroxy(lower)alkyl, and $R^1$, $R^2$, $R^4$, $R^7$ and n are each defined above, with proviso that at least one of $R_b^3$ and $R_a^6$ is always esterified carboxy, or $R_a^5$ is esterified carboxy or esterified carboxy(lower)alkyl, to give a compound of the formula or its salt:

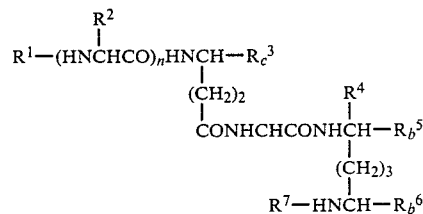

wherein $R_c^3$ and $R_b^6$ are each carboxy, protected carboxy excepting esterified carboxy, carbamoyl or hydroxymethyl, $R_b^5$ is hydrogen, carboxy, protected carboxy excepting esterified carboxy, carbamoyl, carboxy(lower)alkyl or protected carboxy excepting esterified carboxy(lower)alkyl or hydroxy(lower)alkyl, and $R^1$, $R^2$, $R^4$, $R^7$ and n are each as defined above, with proviso that at least one of $R_c^3$ and $R_b^6$ is always hydroxymethyl, or $R_b^5$ is hydroxy(lower)alkyl, or (3) subjecting a compound of the formula or its salt:

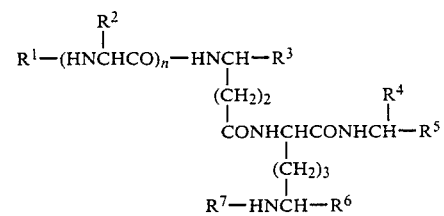

wherein $R^1$, $R^2$, $R^3$, $R^4$, $R^5$, $R^6$, $R^7$ and n are each as defined above, with proviso that at least one of $R^3$ and $R^6$ is protected carboxy, or $R^5$ is protected carboxy or protected carboxy(lower)alkyl, or $R^7$ is an amino protective group, to elimination reaction of protective group(s) to give a compound of the formula or its salt:

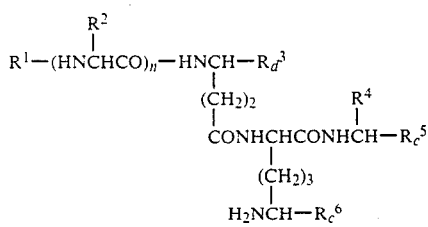

wherein $R_d^3$ and $R_c^6$ are each carboxy, carbamoyl or hydroxymethyl, $R_c^5$ is hydrogen, carboxy, carbamoyl, carboxy(lower)alkyl or hydroxy(lower)alkyl, and $R^1$, $R^2$, $R^4$ and n are each as defined above, with proviso that in the restricted case that each of $R_d^3$ and $R_c^6$ is not simultaneously hydroxymethyl, $R_c^5$ is always hydroxy(lower)alkyl.

8. The compound according to claim 2, wherein $R^1$ is heptanoyl, $R^3$ is carboxy, $R^4$ is hydrogen, $R^5$ is hydroxymethyl, $R^6$ is carboxy, $R^7$ is hydrogen, and n is 0.

9. The compound according to claim 2, wherein $R^1$ is heptanoyl, $R^3$ is carboxy, $R^4$ is hydrogen, $R^5$ is hydroxymethyl, $R^6$ is methoxycarbonyl, $R^7$ is hydrogen, and n is 0.

* * * * *

UNITED STATES PATENT AND TRADEMARK OFFICE
CERTIFICATE OF CORRECTION

PATENT NO. : 4,497,729

DATED : February 5, 1985

INVENTOR(S) : Kitaura et al.

It is certified that error appears in the above-identified patent and that said Letters Patent is hereby corrected as shown below: Title page, Item [75] should read:

- - [75] Inventors:  Yoshihiko Kitaura, Sakurai;
Osamu Nakaguchi, Toyonaka;
Keiji Hemmi, Suita;
Satoshi Yonishi, Kadoma;
Hidekazu Takeno, Tenri;
Satoshi Okada, Takatsuki;
Masashi Hashimoto, Takarazuka,
all of Japan - -

Signed and Sealed this

Eleventh Day of June 1985

[SEAL]

Attest:

DONALD J. QUIGG

*Attesting Officer*  *Acting Commissioner of Patents and Trademarks*